US00PP22965P2

(12) United States Plant Patent
Jupp

(10) Patent No.: US PP22,965 P2
(45) Date of Patent: Aug. 14, 2012

(54) ***DIANELLA* PLANT NAMED 'ALLYN-CITATION'**

(50) Latin Name: *Dianella revoluta*
Varietal Denomination: Allyn-Citation

(75) Inventor: Noel Jupp, East Gresford (AU)

(73) Assignee: VF + NC Jupp, East Gresford, NSW (AU)

( * ) Notice: Subject to any disclaimer, the term of this patent is extended or adjusted under 35 U.S.C. 154(b) by 0 days.

(21) Appl. No.: 12/804,922

(22) Filed: Jul. 30, 2010

(51) Int. Cl.
*A01H 5/00* (2006.01)

(52) U.S. Cl. ..... Plt./424

(58) Field of Classification Search ..... Plt./424
See application file for complete search history.

(56) References Cited

OTHER PUBLICATIONS

Plant Varieties Journal. Quarter One 2011, vol. 24, No. 1, 2011 pp. 241-244.*

Pluto Plant Variety Database 2011/06, retrieved on Mar. 27, 2012. Retrieved at <http://www.upov.int/pluto/en/> Citation for *Dianella* 'Allyn-Citation', 2 pp.*

* cited by examiner

*Primary Examiner* — June Hwu
(74) *Attorney, Agent, or Firm* — C. A. Whealy

(57) ABSTRACT

A new and distinct cultivar of *Dianella* plant named 'Allyn-Citation', characterized by its compact, upright and slightly outwardly slanting plant habit; dense growth habit; narrow and stiff leaves arranged in an upright basal rosette; grey green-colored leaves; and durability with good garden performance.

3 Drawing Sheets

Botanical designation: *Dianella revoluta.*
Cultivar denomination: 'ALLYN-CITATION'.

BACKGROUND OF THE INVENTION

The present invention relates to a new and distinct cultivar of *Dianella* plant, botanically known as *Dianella revoluta*, and hereinafter referred to by the name 'Allyn-Citation'.

The new *Dianella* plant is a product of a breeding program conducted by the Inventor in East Gresford, New South Wales, Australia. The objective of the breeding program is to create new compact *Dianella* plants with grey green-colored narrow leaves.

The new *Dianella* plant originated from a cross-pollination made by the Inventor on Sep. 20, 2003 in East Gresford, New South Wales, Australia of two unnamed selections of *Dianella revoluta*, not patented. The new *Dianella* plant was discovered and selected by the Inventor as a single plant from within the progeny of the stated cross-pollination in a controlled environment in East Gresford, New South Wales, Australia in March, 2004.

Asexual reproduction of the new *Dianella* plant by divisions in East Gresford, New South Wales, Australia since Oct. 10, 2005, has shown that the unique features of this new *Dianella* plant are stable and reproduced true to type in successive generations.

SUMMARY OF THE INVENTION

Plants of the new *Dianella* have not been observed under all possible environmental conditions. The phenotype may vary somewhat with variations in environment such as temperature and light intensity, without, however, any variance in genotype.

The following traits have been repeatedly observed and are determined to be the unique characteristics of 'Allyn-Citation'. These characteristics in combination distinguish 'Allyn-Citation' as a new and distinct cultivar of *Dianella* plant:

1. Compact, upright and slightly outwardly slanting plant habit.
2. Dense growth habit.
3. Narrow and stiff leaves arranged in an upright basal rosette.
4. Grey green-colored leaves.
5. Durable with good garden performance.

Plants of the new *Dianella* differ from plants of the female parent selection in the following characteristics:

1. Plants of the new *Dianella* are more compact than plants of the female parent selection.
2. Plants of the new *Dianella* are more erect than and not as weeping as plants of the female parent selection.
3. Plants of the new *Dianella* are denser than and not as open as plants of the female parent selection.
4. Leaves of plants of the new *Dianella* are more narrow than leaves of plants of the female parent selection.

Plants of the new *Dianella* differ from plants of the male parent selection in the following characteristics:

1. Plants of the new *Dianella* are more compact than plants of the male parent selection.
2. Plants of the new *Dianella* are denser than and not as open as plants of the male parent selection.
3. Leaves of plants of the new *Dianella* are more narrow than leaves of plants of the male parent selection.
4. Plants of the new *Dianella* and the male parent selection differ in leaf color as plants of the male parent selection have green-colored leaves.

Plants of the new *Dianella* can be compared to plants of *Dianella revoluta* 'DR5000', disclosed in U.S. Plant Pat. No. 17,719. In side-by-side comparisons conducted in East Gresford, New South Wales, Australia, plants of the new *Dianella* differed primarily from plants of 'DR5000' in the following characteristics:

1. Plants of the new *Dianella* were taller than plants of 'DR5000'.
2. Plants of the new *Dianella* had slightly narrower leaves than plants of 'DR5000'.
3. Plants of the new *Dianella* and 'DR5000' differed in leaf color as plants of 'DR5000' had dark green-colored leaves.

Plants of the new *Dianella* can also be compared to plants of *Dianella revoluta* 'DRG04', disclosed in U.S. Plant Pat. No. 18,454. In side-by-side comparisons conducted in East Gresford, New South Wales, Australia, plants of the new *Dianella* differed primarily from plants of 'DRG04' in the following characteristics:

1. Plants of the new *Dianella* were more compact than plants of 'DRG04'.
2. Plants of the new *Dianella* had slightly narrower leaves than plants of 'DRG04'.
3. Plants of the new *Dianella* and 'DRG04' differed in leaf color as plants of 'DRG04' had green-colored leaves.

BRIEF DESCRIPTION OF THE PHOTOGRAPHS

The accompanying photographs illustrate the overall appearance of the new *Dianella* plant. These photographs show the colors as true as it is reasonably possible to obtain in colored reproductions of this type. Colors in the photographs may differ slightly from the color values cited in the detailed botanical description which accurately describe the colors of the new *Dianella* plant.

The photograph on the first sheet comprises a side perspective view of a typical plant of 'Allyn-Citation' grown in a container.

The photograph on the second sheet comprises a top perspective view of a typical plant of 'Allyn-Citation' grown in a container.

The photograph on the third sheet comprises a side perspective view of a typical flowering plant of 'Allyn-Citation' grown in an outdoor landscape.

DETAILED BOTANICAL DESCRIPTION

The aforementioned photographs and following observations and measurements describe plants grown during the summer in two-gallon containers in an outdoor nursery in Woodlake, Calif. and under conditions and practices which approximate those generally used in commercial *Dianella* plant production. During the production of the plants, day temperatures ranged from 12° C. to 35° C., night temperatures ranged from 2° C. to 19° C. and light levels averaged 1,000 klux. Plants were 7.5 months old when the photographs and description were taken. In the following description, color references are made to The Royal Horticultural Society Colour Chart, 2007 Edition, except where general terms of ordinary dictionary significance are used.

Botanical classification: *Dianella revoluta* 'Allyn-Citation'.

Parentage:

*Female, or seed, parent*.—Unnamed selection of *Dianella revoluta*, not patented.

*Male, or pollen, parent*.—Unnamed selection of *Dianella revoluta*, not patented.

Propagation:

*Type*.—By divisions.

*Time to initiate roots, summer*.—About 12 to 14 days at temperatures of about 25° C.

*Time to initiate roots, winter*.—About 20 days at temperatures of about 25° C.

*Time to produce a rooted plant, summer*.—About 84 days at temperatures of about 25° C.

*Time to produce a rooted plant, winter*.—About 112 days at temperatures of about 15° C.

*Root description*.—Fine, fibrous; beige in color.

*Rooting habit*.—Freely branching; dense.

Plant description:

*Plant form/growth habit*.—Compact, upright and slightly outwardly slanting plant habit; dense growth habit.

*Plant height*.—About 32 cm.

*Plant diameter or spread*.—About 32 cm.

Foliage description:

*Arrangement*.—Two-ranked, simple; grass-like; sheathing; arranged in a upright basal rosette.

*Length*.—About 34 cm.

*Width, flattened*.—About 6 mm.

*Shape*.—Linear.

*Apex*.—Tapering to a point.

*Margin*.—Entire with minute points.

*Aspect*.—Initially upright then slightly outwardly slanting with development.

*Cross-section*.—Concave.

*Texture, upper and lower surfaces*.—Smooth, glabrous, glaucous; lower surface with spines at the midrib, color, similar to lamina.

*Venation pattern*.—Parallel.

*Color*.—Developing and fully expanded leaves, upper surface: Close to 147A covered with a waxy bloom, close to 189A. Developing and fully expanded leaves, lower surface: Close to 147A covered with a waxy bloom, close to 189A. Venation, upper and lower surfaces: Similar to leaf surface color.

Inflorescence description: Inflorescence and flower development has rarely been observed on plants of the new *Dianella*. Flower initiation and development typically occurs during the autumn in Australia and plants typically do not flower until the second year of production. When present, the panicled flowers are blue, close to 104B, in color and the mature fruits are also blue, close to 104B, in color. Other inflorescence, flower bud, flower and fruit characteristics are similar to other cultivars and selections of *Dianella revoluta* that initiate and develop flowers known to the Inventor.

Disease/pest resistance: Plants of the new *Dianella* have not been shown to be resistant to pathogens and pests common to *Dianella*.

Garden performance: Plants of the new *Dianella* have been observed to have good garden performance and tolerate wind, rain and temperatures ranging from about 0° C. to about 45° C.

It is claimed:

1. A new and distinct *Dianella* plant named 'Allyn-Citation' as illustrated and described.

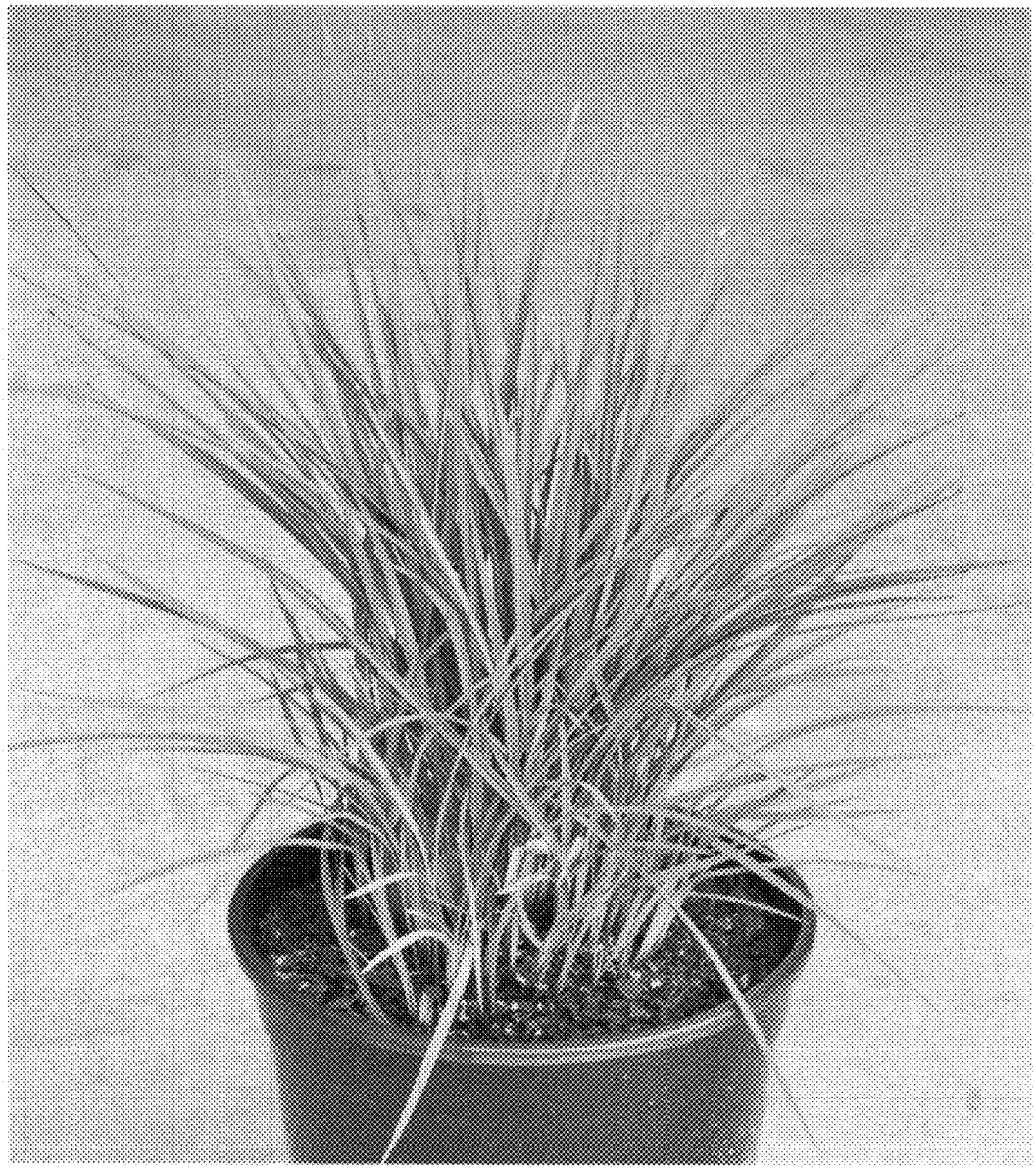

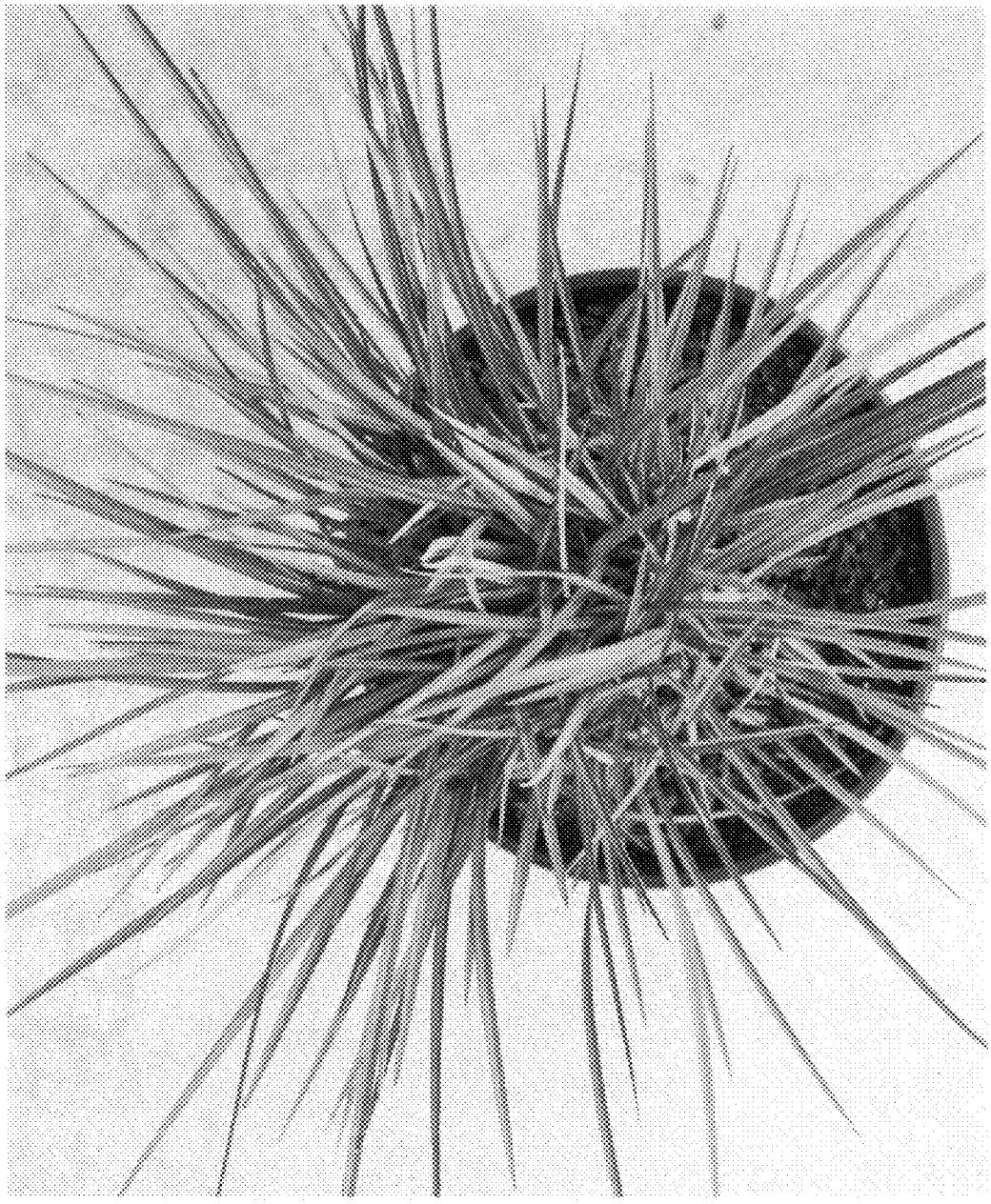

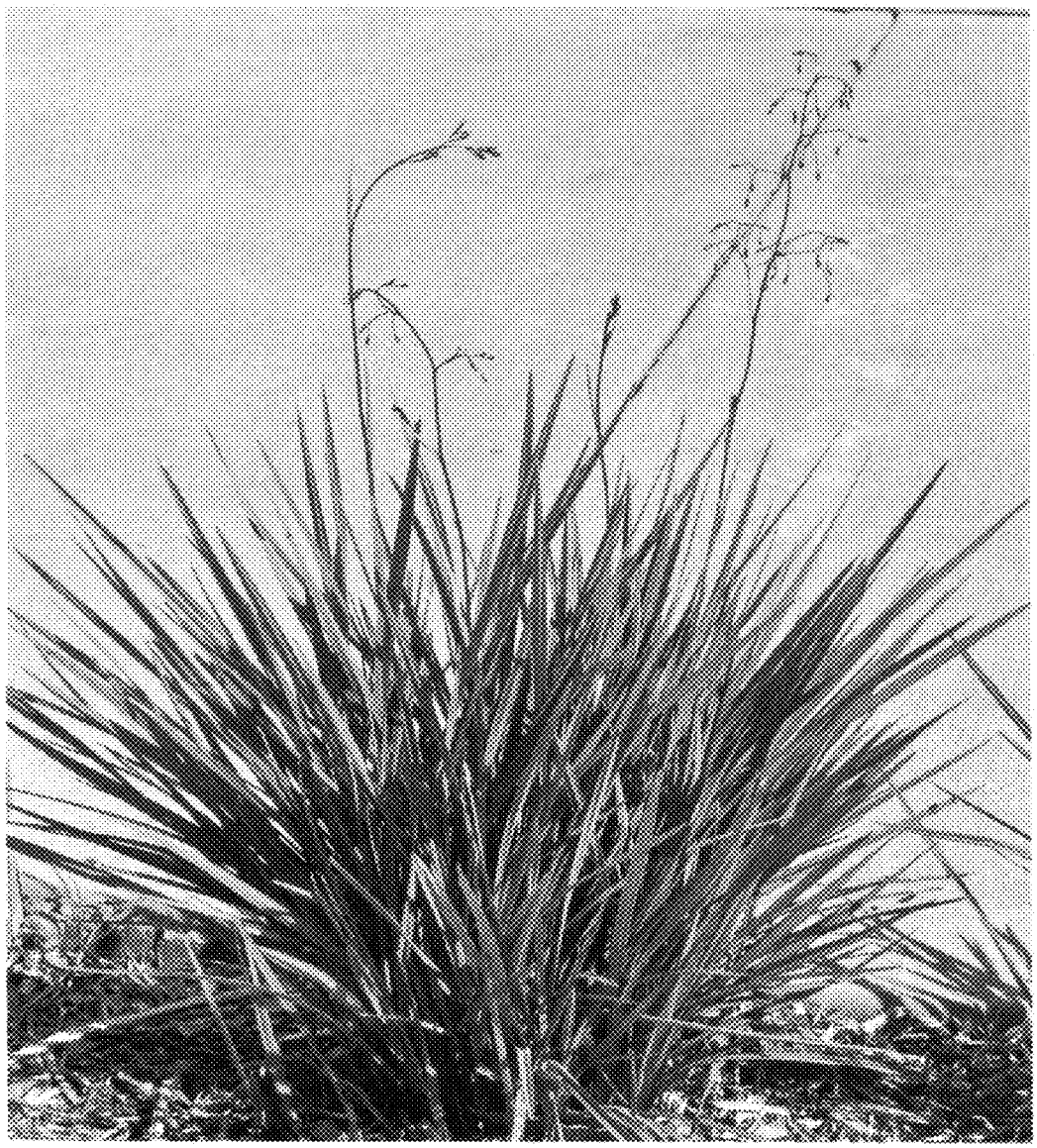

* * * * *